United States Patent
Mamedov et al.

(10) Patent No.: US 7,186,670 B2
(45) Date of Patent: Mar. 6, 2007

(54) PROCESS FOR THE AMMOXIDATION OF ALKANES AND OLEFINS

(75) Inventors: Edouard A. Mamedov, Houston, TX (US); Kathleen A. Bethke, Sugar Land, TX (US); Shahid N. Shaikh, Houston, TX (US); Armando Araujo, Houston, TX (US); Neeta K. Kulkarni, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 171 days.

(21) Appl. No.: 10/955,550

(22) Filed: Sep. 30, 2004

(65) Prior Publication Data

US 2006/0069279 A1   Mar. 30, 2006

(51) Int. Cl.
*B01J 23/20* (2006.01)

(52) U.S. Cl. .................................................... 502/353

(58) Field of Classification Search ..................... None
See application file for complete search history.

(56) References Cited

U.S. PATENT DOCUMENTS 6,710,011 B2 * 3/2004 Mamedov et al. .......... 502/353

* cited by examiner

*Primary Examiner*—Kamal A. Saeed
*Assistant Examiner*—Andrew B. Freistein
(74) *Attorney, Agent, or Firm*—Jim Wheelington

(57) ABSTRACT

A process for the vapor phase ammoxidation of alkanes and olefins with a catalyst of the general empirical formula:

$$VSb_aM_bQ_cO_x$$

wherein M is at least one element selected from magnesium, aluminum, zirconium, silicon, hafnium, titanium and niobium, Q is at least one element selected from rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, a is 0.5 to 20, b is 2 to 50, c is 0 to 10 and x is determined by the valence requirements of the elements present. The process has a co-feed of gaseous carbon dioxide with an alkane (paraffin) and/or alkene, ammonia and an oxygen-containing gas which react in the presence of the catalyst to form a nitrile and by-products.

26 Claims, No Drawings

PROCESS FOR THE AMMOXIDATION OF ALKANES AND OLEFINS

BACKGROUND OF THE INVENTION

1. Field of the Invention

The invention relates to a process for the catalytic ammoxidation of alkanes and olefins, more specifically $C_3$ to $C_5$ paraffins or olefins, such as propane or isobutane and propylene or isobutylene, to the corresponding $\alpha,\beta$-unsaturated mononitriles, e.g., acrylonitrile and methacrylonitrile.

2. Description of the Prior Art

U.S. Pat. No. 6,710,207 discloses a method for producing an unsaturated carboxylic acid or an unsaturated nitrile, such as acrylic acid or acrylonitrile, by vapor phase catalytic oxidation of mixtures of alkenes and alkanes in the presence of a mixed metal oxide catalyst. Carbon dioxide is disclosed as an impurity in the feed, as a diluting gas for adjusting the space velocity and the oxygen partial pressure and as a by-product of the reaction.

U.S. Pat. No. 3,535,366 discloses a process for the production of terephthalonitrile by including an inert heat carrier gas, such as methane, ethane or carbon dioxide, which has a heat capacity higher than that of nitrogen to reduce hot spot temperature which results in improved selectivity. The heat carrier gas is present from 5 to 80%, preferably 5 to 40%, by volume.

U.S. Pat. No. 6,080,882 discloses a process for producing acrylonitrile or methacrylonitrile from propane or isobutane by ammoxidation in which the temperature is elevated to the ammoxidation reaction temperature while a molecular oxygen-containing gas and a combustible gas are supplied to the reaction zone. The molecular oxygen-containing gas may be diluted with an inert gas, such as nitrogen, argon, steam or carbon dioxide.

U.S. Pat. No. 5,015,576 discloses a process for production of nitrites from hydrocarbons by reaction with an oxygen-containing gas, such as oxygen, air or a gas enriched in oxygen, and ammonia in the presence of a catalyst and a gaseous flame suppressor. The gaseous flame suppressor contains a substantially unreactive hydrocarbon having from 1 to 5 carbon atoms, carbon dioxide and, where air or enriched air is utilized as the oxygen-containing gas in the feed to the ammoxidation reactor, nitrogen.

Prior art discloses the addition of certain compounds to the feed to improve catalyst performance. U.S. Pat. No. 3,746,737 discloses a process for the production of acrylonitrile or methacrylonitrile by vapor phase reaction of a mixture of a hydrocarbon, such as propane or isobutane, ammonia and oxygen in the presence of a Mo—Ce catalyst and a halogen or a halide compound for improved conversion and selectivity.

U.S. Pat. No. 3,833,638 discloses preparation of acrylonitrile or methacrylonitrile from a mixture of propane or isobutane, ammonia and oxygen in the presence of a Mo—Ce catalyst optionally in the presence of a halogen or a halide compounds or sulfur or hydrogen sulfide for improved conversion and selectivity.

U.S. Pat. Nos. 4,000,178, 4,101,188 and 5,576,469 also disclose the addition of halide compounds as promoters in an ammoxidation reaction using antimony-containing catalysts. U.S. Pat. No. 3,696,267 also discloses sulfur in the ammoxidation of saturated hydrocarbons using an antimony-uranium catalyst to improve conversion and yield of unsaturated nitriles.

U.S. Pat. Nos. 5,332,855 and 5,334,743 disclose ammoxidation of alkanes, such as propane, from a reactive gas of saturated hydrocarbon, ammonia, oxygen and an inert diluent and/or steam.

While carbon dioxide had been disclosed as present in a process for the ammoxidation of an alkane to an unsaturated nitrile, carbon dioxide has not been disclosed as beneficial to the selectivity to the nitrile product.

SUMMARY OF THE INVENTION

The present invention provides a vapor phase process for the ammoxidation of paraffins or olefins to unsaturated mononitriles, in particular the ammoxidation of propane and/or propylene and isobutane and/or isobutylene to acrylonitrile and methacrylonitrile, respectively. Gaseous carbon dioxide is co-fed with a hydrocarbon, ammonia and an oxygen-containing gas over a mixed metal oxide catalyst containing oxides of vanadium, antimony and other metals to improve selectivity.

DESCRIPTION OF EMBODIMENTS OF THE INVENTION

In the ammoxidation process of the present invention, the reaction is run in the gas phase by contacting a mixture containing paraffin, ammonia, molecular oxygen and a diluent in a fixed bed of catalyst, or a fluidized bed, or a moving bed (riser reactor). The mole ratio of paraffin to ammonia is usually in the range from 0.5 to 10, preferably from 1 to 2.5, and the mole ratio of paraffin to oxygen is usually from 0.05 to 10, preferably from 0.5 to 2. The mole ratio of gaseous diluent, e.g., $N_2$, He, and Ar, to paraffin usually ranges from 0.5 to 20, preferably from 0.5 to 2. Higher molar ratios can be used but are usually uneconomical. In the present invention, carbon dioxide replaces some or all of the diluent. Carbon dioxide is present in the amount of between 0.1 to 40 mol %, preferably 10 to 40 mol %, more preferably 20 to 40 mol % or at a mole ratio of carbon dioxide to paraffin of between 0.05 to 2, preferably 0.5 to 2.

In the present process, the paraffin as the starting material is not particularly limited, and it may be any lower alkane having from 2 to 8 carbon atoms. However, from the viewpoint of industrial application of the obtainable nitriles, it is preferred to employ propane or isobutane. Low-weight olefins, such as propylene and isobutylene, can also be employed for production of acrylonitrile and methacrylonitrile, respectively. The process according to the invention is more particularly suitable for the ammoxidation of propane.

The reaction temperature range can vary from 350 to 550° C., preferably from 425 to 500° C. The latter temperature range is especially useful in the case of propane ammoxidation to acrylonitrile.

The pressure of the reaction can be greater than or equal to atmospheric pressure and can range from 1 to 40 psig. Preferably, pressure is 1 to 20 psig.

The effective contact time is in the range from 0.01 to 10 seconds, but is preferably from 0.05 to 8 seconds, more preferably from 0.1 to 5 seconds.

The most advantageous combination of temperature, pressure and contact time for a given desired result from a given feed can be determined by routine experimentation.

The catalyst of the present invention is of the general empirical formula:

$$VSb_aM_bQ_cO_x$$

wherein M is at least one element selected from magnesium, aluminum, zirconium, silicon, hafnium, titanium and niobium, Q is at least one element selected from rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, a is 0.5 to 20, b is 2 to 50, c is 0 to 10 and x is determined by the valence requirements of the elements present.

The present invention is described in further detail in the following Examples. However, it should be understood that the present invention is by no means restricted to such specific Examples.

Examples 1–3 and Comparative Example 1

Catalyst of Nominal Composition
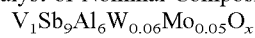
$V_1Sb_9Al_6W_{0.06}Mo_{0.05}O_x$ 34.3 g of $Al(NO_3)_3.9H_2O$ were dissolved in 270 ml of deionized water at room temperature. The pH was adjusted to 8.0 by the addition of 30 Wt. % $NH_4OH$ to obtain a white gel. 30.8 g of $SbCl_3$ were placed in a 300 ml of deionized water and stirred vigorously for 30 minutes to obtain a milky-white suspension. 1.75 g of $NH_4VO_3$ dissolved at 80° C. in 75 ml of water was added to the suspension. Then 30% $NH_4OH$ was added dropwise to the suspension while vigorously stirring to adjust the pH to 8.0. The resultant brown-green suspension was added to the previously prepared aluminum gel at pH 8.0 and stirred for an hour. The precipitate was filtered and squeezed into a light gray-green cake. The paste-like material was transferred to a porcelain dish, dried and calcined in air under the following conditions: room temperature to 120° C. at 5° C./min, held for 5 hours, temperature increased to 430° C. at 20° C./min, held for 4 hours, temperature increased to 650° C. at 20° C./min and held for 6.5 hours. The calcined material was cooled down and ground to a fine powder of base material.

10 g of base material were immersed in a clear mixed solution of ammonium paramolybdate and ammonium tungstate prepared by dissolving 0.051 g $(NH_4)_6Mo_7O_{24}$ and 0.086 g $(NH_4)_2WO_4$ in 10 ml of deionized water at 80° C. Under constant stirring and heating on a hot plate, the water was evaporated until a freeflowing green powder was obtained. The green powder was dried at 120° C. for 5 hours followed by calcination at 430° C. for 4 hours and at 650° C. for 4.5 hours. The catalyst thus obtained was pressed, crushed and sieved to 18–30 mesh.

3.8 cc of the catalyst mixed with 8.2 cc of quartz chips were loaded in a ½ inch I.D. silica-coated stainless steel fixed bed reactor and tested for the ammoxidation of propane at atmospheric pressure, at 475° C. and 500° C. and at a flow rate of 200 m/min. The feed was 23% $C_3H_8$, 10% $NH_3$, 27% $O_2$ and 0, 10, 20 and 40 mole % of carbon dioxide (Comparative Example 1, Example 1, Example 2 and Example 3) with the balance He. Reaction products were analyzed by on-line gas chromatography. The results are shown in Table 1 where T, τ and ACN denote reaction temperature, contact time and acrylonitrile, respectively.

Examples 4–6 and Comparative Example 2

Catalyst of Nominal Composition
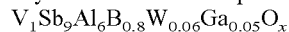
$V_1Sb_9Al_6B_{0.8}W_{0.06}Ga_{0.05}O_x$ The base material was prepared as in Example 1 above. A clear solution of boric acid and ammonium tungstate was prepared by dissolving and mixing 0.554 g $H_3BO_3$ and 0.191 g $(NH_4)_2WO_4$ in 10 ml of deionized water at 80° C. 10 g of the base material was immersed in the clear solution. Under constant stirring and heating on a hot plate, the water was evaporated until a freeflowing powder was obtained. 0.143 g of gallium nitrate dissolved in 5 ml of deionized water was mixed with the powder. The water was evaporated as above to obtain a green powder. The green powder was dried at 120° C. for 5 hours followed by calcination at 430° C. for 4 hours and at 650° C. for 4.5 hours. After cooling, the catalyst thus obtained was pressed, crushed and sieved to 18–30 mesh.

3 cc of the catalyst mixed with 9 cc of quartz chips were loaded in a ½ inch I.D. silica-coated stainless steel fixed bed reactor and tested for the ammoxidation of propane at atmospheric pressure, at 475° C. and 500° C. and at a flow rate of 100–130 ml/min. The feed was 23% $C_3H_8$, 10% $NH_3$, 27% $O_2$ and 0, 10, 20 and 40 mole % of carbon dioxide (Comparative Example 2, Example 4, Example 5 and Example 6) with the balance He. Reaction products were analyzed by on-line gas chromatography. The results are shown in Table 1 where T, τ and ACN denote reaction temperature, contact time and acrylonitrile, respectively.

Examples 7–9 and Comparative Example 3

Catalyst of Nominal Composition
$V_1Sb_{10}Mg_3W_{0.05}O_x$ 5.27 g of $NH_4VO_3$ were dissolved in 200 ml of deionized water at 80° C. and 65.5 g of $Sb_2O_3$ were dissolved in 280 ml diluted nitric acid with a $HNO_3$ to $H_2O$ volume ratio of 1:3. The antimony oxide solution was added to the ammonium metavanadate solution and the heat was turned off. After stirring the mixture for 30 minutes, the pH was adjusted to 8.0 by adding dropwise a 30% solution of ammonium hydroxide which caused a color change in the solution from green to brown.

35.2 g of $Mg(NO_3)_2.6H_2O$ were dissolved in 530 ml of deionized water and 30% $NH_4OH$ was added dropwise with stirring to adjust pH to 10. This solution was mixed with the solution containing the antimony and vanadium compounds and the resulting mixture was heated on a hot plate with stirring until the solvent evaporated to give a thick slurry. The slurry was heated in an oven at 120° C. for 24 hours to produce dried base material.

0.51 g of $(NH_4)_2WO_4$ was dissolved in 100 ml of deionized water. 72.8 g of the base material were immersed in the ammonium tungstate solution. The mixture was stirred in an uncovered ceramic dish with heating to evaporate the water. When the mixture could no longer be stirred, it was dried overnight in an oven at 120° C. after which it was transferred to a muffle furnace with flowing air with the temperature being increased at 5° C./min to 100° C., then at 0.9° C./min to 800° C. and held at this temperature for 3 hours for calcination. The calcined catalyst was cooled, pressed and sieved to collect the 18–30 mesh particles.

3.2 cc of the catalyst mixed with 8.8 cc of quartz chips were loaded in a ½ inch I.D. silica-coated stainless steel fixed bed reactor and tested for the ammoxidation of propane at atmospheric pressure, at 475° C. and 500° C. and at a flow rate of 100 ml/min. The feed was 23% $C_3H_8$, 10% $NH_3$, 27% $O_2$ and 0, 10, 20 and 40 mole % of carbon dioxide (Comparative Example 3, Example 7, Example 8 and Example 9) with the balance He. Reaction products were analyzed by on-line gas chromatography. The results are shown in Table 1 where T, τ and ACN denote reaction temperature, contact time and acrylonitrile, respectively.

Examples 10–12 and Comparative Example 4

Catalyst of nominal composition $V_1Sb_{1.4}Sn_{0.2}Ti_{0.1}O_x$

A 1 L beaker was placed in an oil bath and equipped with a magnetic stir bar. 450 ml of deionized water and 50 ml of 30 wt % of $H_2O_2$ were added to the beaker. 13.67 g of $V_2O_5$ were added to the solution with stirring for approximately 30 minutes during which the solution turned from orange to dark red in color. 30.66 g of $Sb_2O_3$ and 1.21 g of $TiO_2$ were added to the solution. The beaker was covered with a watch glass and the solution was boiled for 3 hours during which deionized water was added as necessary to keep the volume of solution constant and the color of the solution changed from golden yellow to bright yellow to olive green and to black. 9.18 g Sn (II) tartrate were added to the solution. The mixture was boiled down until a paste remained. The paste was dried overnight in an oven at 120° C., crushed and calcined in a muffle furnace with air flow. The temperature was raised to 100° C. at 5° C./min and then to 325° C. at 2° C./min, held for 1 hour, increased to 650° C. at 2° C./min and held for 8 hours. The catalyst was pressed, sieved to 18–30 mesh and placed back in the muffle furnace in a flow of air. The temperature was raised to 600° C. at 10° C./min, to 820° C. at 2° C./min, held at 820° C. for 3 hours, cooled to 650° C. at 10° C./min and held for 3 hours. The calcined catalyst was placed in a filter funnel with a quartz frit and rinsed with 6.25 ml isobutanol/g. This wash was repeated twice more after which the catalyst was placed in an oven and dried at 120° C.

3 cc of the catalyst mixed with 9 cc of quartz chips were loaded in a ½ inch I.D. silica-coated stainless steel fixed bed reactor and tested for the ammoxidation of propane at atmospheric pressure, at 475° C. and 500° C. and at a flow rate of 60 ml/min. The feed was 23% $C_3H_8$, 10% $NH_3$, 27% $O_2$ and 0, 10, 20 and 40 mole % of carbon dioxide (Comparative Example 4, Example 10, Example 11 and Example 12) with the balance He. Reaction products were analyzed by on-line gas chromatography. The results are shown in Table 1 where T, τ and ACN denote reaction temperature, contact time and acrylonitrile, respectively.

Comparative Example 5

Non-catalytic propane ammoxidation was carried out at atmospheric pressure and 500° C. in a ½ inch I.D. silica-coated stainless steel fixed bed reactor filled with 12 cc of quartz chips. The feed of 100 ml/min was 23% $C_3H_8$, 10% $NH_3$, 27% $O_2$ and 40 mole % of He. Reaction products were analyzed by on-line gas chromatography. The results are shown in Table 1 where T, τ and ACN denote reaction temperature, contact time and acrylonitrile, respectively.

Comparative Example 6

Non-catalytic propane ammoxidation was carried out at atmospheric pressure and 500° C. in a ½ inch I.D. silica-coated stainless steel fixed bed reactor filled with 12 cc of quartz chips. The feed of 100 ml/min was 23% $C_3H_8$, 10% $NH_3$, 27% $O_2$ and 40 mole % of $CO_2$. Reaction products were analyzed by on-line gas chromatography. The results are shown in Table 1 where T, τ and ACN denote reaction temperature, contact time and acrylonitrile, respectively.

TABLE 1

| Example | Catalyst | $CO_2$ (mol %) | T (° C.) | τ (sec.) | Conversion (%) | Selectivity ACN | HCN | $CO_x$ |
|---|---|---|---|---|---|---|---|---|
| 1 | $V_1Sb_9Al_6W_{0.06}Mo_{0.05}O_x$ | 10 | 475 | 1.1 | 13.2 | 57.5 | 19.8 | 17.4 |
|   |   |   | 500 | 1.1 | 19.7 | 63.4 | 15.2 | 17.5 |
| 2 | $V_1Sb_9Al_6W_{0.06}Mo_{0.05}O_x$ | 20 | 475 | 1.1 | 11.9 | 62.6 | 21.9 | 9.8 |
|   |   |   | 500 | 1.1 | 18.0 | 66.3 | 16.6 | 13.5 |
| 3 | $V_1Sb_9Al_6W_{0.06}Mo_{0.05}O_x$ | 40 | 475 | 1.1 | 10.7 | 67.6 | 23.6 | 3.2 |
|   |   |   | 500 | 1.1 | 16.9 | 72.2 | 18.2 | 5.3 |
| Comp. 1 | $V_1Sb_9Al_6W_{0.06}Mo_{0.05}O_x$ | 0 | 475 | 1.1 | 12.7 | 57.5 | 19.5 | 17.8 |
|   |   |   | 500 | 1.1 | 19.2 | 62.0 | 14.8 | 19.8 |
| 4 | $V_1Sb_9Al_6B_{0.8}W_{0.06}Ga_{0.05}O_x$ | 10 | 475 | 1.8 | 15.8 | 59.6 | 17.5 | 18.1 |
|   |   |   | 500 | 1.8 | 24.3 | 61.4 | 12.9 | 22.8 |
| 5 | $V_1Sb_9Al_6B_{0.8}W_{0.06}Ga_{0.05}O_x$ | 20 | 475 | 1.6 | 15.8 | 61.2 | 18.1 | 15.7 |
|   |   |   | 500 | 1.6 | 24.2 | 62.6 | 13.3 | 21.0 |
| 6 | $V_1Sb_9Al_6B_{0.8}W_{0.06}Ga_{0.05}O_x$ | 40 | 475 | 1.4 | 14.0 | 69.5 | 21.0 | 8.4 |
|   |   |   | 500 | 1.4 | 22.3 | 69.9 | 15.2 | 11.4 |
| Comp. 2 | $V_1Sb_9Al_6B_{0.8}W_{0.06}Ga_{0.05}O_x$ | 0 | 475 | 1.8 | 16.5 | 56.6 | 16.7 | 22.0 |
|   |   |   | 500 | 1.8 | 25.8 | 58.3 | 12.2 | 26.7 |
| 7 | $V_1Sb_{10}Mg_3W_{0.05}O_x$ | 10 | 475 | 1.9 | 23.2 | 53.9 | 22.7 | 18.4 |
|   |   |   | 500 | 1.9 | 29.2 | 61.8 | 17.1 | 16.9 |
| 8 | $V_1Sb_{10}Mg_3W_{0.05}O_x$ | 20 | 475 | 1.9 | 19.3 | 59.1 | 23.5 | 12.5 |
|   |   |   | 500 | 1.9 | 28.0 | 64.7 | 17.0 | 12.7 |
| 9 | $V_1Sb_{10}Mg_3W_{0.05}O_x$ | 40 | 475 | 1.9 | 17.0 | 64.3 | 27.4 | 9.8 |
|   |   |   | 500 | 1.9 | 27.5 | 69.8 | 19.7 | 11.4 |
| Comp. 3 | $V_1Sb_{10}Mg_3W_{0.05}O_x$ | 0 | 475 | 1.9 | 19.5 | 54.5 | 21.9 | 18.9 |
|   |   |   | 500 | 1.9 | 29.2 | 61.5 | 15.7 | 18.4 |
| 10 | $V_1Sb_{1.4}Sn_{0.2}Ti_{0.1}O_x$ | 10 | 475 | 3.0 | 7.9 | 71.3 | 13.0 | 9.2 |
|   |   |   | 500 | 3.0 | 13.9 | 68.3 | 11.2 | 12.0 |
| 11 | $V_1Sb_{1.4}Sn_{0.2}Ti_{0.1}O_x$ | 20 | 475 | 3.0 | 7.5 | 72.7 | 13.2 | 7.1 |
|   |   |   | 500 | 3.0 | 13.3 | 73.0 | 12.1 | 10.4 |
| 12 | $V_1Sb_{1.4}Sn_{0.2}Ti_{0.1}O_x$ | 40 | 475 | 3.0 | 7.9 | 74.3 | 13.3 | 5.6 |
|   |   |   | 500 | 3.0 | 13.7 | 74.1 | 12.3 | 9.1 |

TABLE 1-continued

| Example | Catalyst | CO$_2$ (mol %) | T (° C.) | τ (sec.) | Conversion (%) | Selectivity ACN | HCN | CO$_x$ |
|---|---|---|---|---|---|---|---|---|
| Comp. 4 | V$_1$Sb$_{1.4}$Sn$_{0.2}$Ti$_{0.1}$O$_x$ | 0 | 475 | 3.0 | 8.2 | 68.2 | 12.0 | 13.4 |
|  |  |  | 500 | 3.0 | 14.8 | 71.7 | 9.9 | 14.0 |
| Comp. 5 | None | 0 | 475 | 7.2 | — | — | — | — |
|  |  |  | 500 | 7.2 | 0.3 | — | — | 38.9* |
| Comp. 6 | None | 40 | 475 | 7.2 | 0.1 | — | — | — |
|  |  |  | 500 | 7.2 | 0.3 | — | — | 35.2* |

*Propylene was also produced with selectivities of 61.1% and 64.8%

The data above demonstrates the efficacy of a carbon dioxide co-feed in a process for ammoxidation of alkanes and olefins with ammonia, molecular oxygen and a diluent in the gas phase with a vanadium-antimony based catalyst wherein the diluent is all or in part carbon dioxide.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for ammoxidation of alkanes and olefins comprising:
   contacting a mixture of an alkane or olefin, ammonia, molecular oxygen and a diluent in the gas phase with a catalyst composition of the formula;

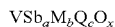
   VSb$_a$M$_b$Q$_c$O$_x$ wherein V is vanadium, Sb is antimony, M is at least one element selected from magnesium, aluminum, zirconium, silicon, hafnium, titanium and niobium, Q is at least one element selected from rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, a is 0.5 to 20, b is 2 to 50, c is 0 to 10 and x is determined by the valence requirements of the elements present;
   wherein the diluent comprises carbon dioxide from 0.1 to 40 mole % of the mixture.

2. The process of claim 1 wherein the catalyst is in a fixed bed, fluidized bed or a moving bed.

3. The process of claim 1 wherein the mole ratio of alkane to ammonia is in the range from 0.5 to 10.

4. The process of claim 3 wherein the mole ratio of alkane to ammonia is in the range from 1 to 2.5.

5. The process of claim 4 wherein the mole ratio of alkane to oxygen is in the range from 0.1 to 10.

6. The process of claim 5 wherein the mole ratio of alkane to oxygen is in the range from 0.5 to 2.

7. The process of claim 1 wherein the diluent is carbon dioxide and at least one selected from the group consisting of nitrogen, helium, argon and water.

8. The process of claim 1 wherein the mole ratio of diluent to alkane is in the range from 0.05 to 20.

9. The process of claim 8 wherein the mole ratio of diluent to alkane is in the range from 0.5 to 2.

10. The process of claim 1 wherein the mole ratio of carbon dioxide to alkane is in the range from 0.05 to 2.

11. The process of claim 10 wherein the mole ratio of carbon dioxide to alkane is in the range from 0.5 to 2.

12. The process of claim 1 wherein the alkane has from two to eight carbon atoms.

13. The process of claim 1 wherein the alkane is propane or isobutane.

14. The process of claim 1 wherein the contact occurs at a temperature range from 350 to 550° C.

15. The process of claim 14 wherein the temperature is from 425° to 500° C.

16. The process of claim 1 wherein the contact occurs at a pressure from 1 to 40 psig.

17. The process of claim 16 wherein the pressure is from 1 to 20 psig.

18. The process of claim 17 wherein the pressure is atmospheric.

19. The process of claim 1 wherein the contact time is from 0.01 to 10 seconds.

20. The process of claim 19 wherein the contact time is from 0.05 to 8 seconds.

21. The process of claim 20 wherein the contact time is from 0.1 to 5 seconds.

22. The process of claim 1 wherein carbon dioxide in the range from 10 mole % to 40 mole %.

23. The process of claim 22 wherein carbon dioxide in the range from 20 mole % to 40 mole %.

24. A process for ammoxidation of alkanes and olefins comprising:
   co-feeding a diluent in the gas phase with a mixture of an alkane or olefin, ammonia, molecular oxygen to react in the presence of a catalyst composition of the formula;

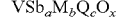
   VSb$_a$M$_b$Q$_c$O$_x$ wherein M is at least one element selected from magnesium, aluminum, zirconium, silicon, hafnium, titanium and niobium, Q is at least one element selected from rhenium, tungsten, molybdenum, tantalum, manganese, phosphorus, cerium, tin, boron, scandium, bismuth, gallium, indium, iron, chromium. lanthanum, yttrium, zinc, cobalt, nickel, cadmium, copper, strontium, barium, calcium, silver, potassium, sodium and cesium, a is 0.5 to 20, b is 2 to 50, c is 1 to 10 and x is determined by the valence requirements of the elements present;
   wherein the diluent comprises carbon dioxide from 0.1 to 40 mole % of the mixture.

25. The process of claim 24 wherein carbon dioxide in the range from 10 mole % to 40 mole %.

26. The process of claim 25 wherein carbon dioxide in the range from 20 mole % to 40 mole %.

* * * * *